United States Patent [19]
Kawata et al.

[11] Patent Number: 5,880,308
[45] Date of Patent: Mar. 9, 1999

[54] PROCESS FOR PREPARING AROMATIC BISPHOSPHATES

[75] Inventors: Shigeru Kawata; Kiyoharu Hirao, both of Osaka; Kazuo Noguchi, Aichi, all of Japan

[73] Assignee: Daihachi Chemical Industry Co., Ltd., Osaka, Japan

[21] Appl. No.: 761,376

[22] Filed: Dec. 9, 1996

[30] Foreign Application Priority Data

Jul. 30, 1996 [JP] Japan .................................... 8-200770

[51] Int. Cl.⁶ ........................................................ C07F 9/12
[52] U.S. Cl. ............................................. 558/99; 558/162
[58] Field of Search ................................................ 558/99

[56] References Cited

U.S. PATENT DOCUMENTS 3,254,973  6/1966  Giammaria et al. ................... 558/99 X
5,122,556  6/1992  Kambour .
5,420,327  5/1995  Bright et al. .

FOREIGN PATENT DOCUMENTS 0509506  10/1992  European Pat. Off. .
218336   4/1990   Japan .
8143584  6/1996   Japan .

OTHER PUBLICATIONS

Kosolapoff et al., "Structural Effects in Reactions of Organophosphorous Compounds. I. Reactions of Phosphorous Oxychloride with Hindered Phenols", *J. Chem. Soc.*, pp. 815–818 (1968).

Stackman, "Phosphorous Based Additives for Flame Retardant Polyester. 2. Polymeric Phosphorous Esters", *Ind. Eng. Chem. Prod. Res. Dev.*, vol. 21, No. 2, pp. 332–336 (1982).

*Primary Examiner*—Michael G. Ambrose
*Attorney, Agent, or Firm*—Greenblum & Bernstein, P.L.C.

[57] ABSTRACT

A process for preparing aromatic bisphosphates includes: a first step of reacting an aromatic monohydroxy compound having a steric hindrance group at the ortho position, with a phosphorus oxyhalide in the presence of a Lewis acid catalyst (a) to yield a reaction mixture containing diarylphosphorohalidate, and a second step of reacting the reaction mixture of the first step with an aromatic dihydroxy compound in the presence of a Lewis acid catalyst (b) to obtain an aromatic bisphosphate, wherein the aromatic monohydroxy compound and the phosphorus oxyhalide are reacted in a molar ratio of 2.0:1.0–1.1 in the first step, and the reaction mixture of the first step is subjected to a distillation treatment before the reaction of the second step, thereby obtaining the aromatic bisphosphate of high purity.

19 Claims, 6 Drawing Sheets

PROCESS FOR PREPARING AROMATIC BISPHOSPHATES

BACKGROUND OF THE INVENTION

1. Field of the Invention

The present invention relates to a process for preparing aromatic bisphosphates. More particularly, the present invention relates to a process for preparing highly pure aromatic bisphosphates having an extremely low content of oligomeric phosphates and triphosphate components, capable of being solidified easily, and being useful as a fire retardant or a plasticizer for a synthetic resin.

2. Description of the Related Arts

Aromatic bisphosphates have characteristics such as low volatility, high temperature stability and no poisonous halogens, so that they are used as a fire retardant or plasticizer for imparting fire retardancy, temperature stability and good moldability to thermoplastic resin or thermosetting resin. Also, aromatic bisphosphates have a resistance to the temperature (about 300° C.) for molding highly functional plastics that have been recently developed.

There are known two methods for preparing aromatic bisphosphates. One method (1) involves reacting an aromatic monohydroxy compound with a phosphorus oxyhalide and then reacting the resultant with an aromatic dihydroxy compound. The other method (2) involves reacting an aromatic dihydroxy compound with a phosphorus oxyhalide and then reacting the resultant with an aromatic monohydroxy compound.

In the method (1), when an aromatic monohydroxy compound having no steric hindrance group at its ortho position is reacted with phosphorus oxychloride, monoarylphosphorodihalidate and triarylphosphate are produced as by-products in addition to the object diarylphosphorohalidate, and also unreacted phosphorus oxyhalide is left as a residue. If the reaction mixture obtained as above without purification is reacted with an aromatic dihydroxy compound, it is not possible to obtain an aromatic bisphosphate of high purity. On the other hand, if the reaction mixture is subjected to a purification process such as distillation, the yield will be extremely lowered, which is economically disadvantageous.

Alternatively, if an aromatic monohydroxy compound having a steric hindrance group at its ortho position is reacted with phosphorus oxyhalide in the method (1), it is not possible to prepare an aromatic bisphosphate of high purity although the aforementioned by-products are produced at a lower ratio.

In the method (2), if a theoretical amount of phosphorus oxyhalide is reacted with an aromatic dihydroxy compound, it is inevitable that an oligomeric phosphate is produced as a by-product. Therefore, the compound obtained by reacting the reaction mixture containing the by-product with an aromatic monohydroxy compound contains a large amount of the oligomeric phosphate, so that the obtained compound will have a resin-like shape. An excess amount of phosphorus oxyhalide used in the reaction reduces only the ratio of the oligomeric phosphate produced as a by-product and does not produce an aromatic bisphosphate of high purity. In addition, the unreacted phosphorus oxyhalide in the reaction mixture must be removed before the reaction with an aromatic monohydroxy compound. Accordingly, the method (2) is not an economical and efficient manufacturing process.

The oligomeric phosphate produced as a by-product is not preferable because it lowers the purity of the object aromatic bisphosphate and, therefore, prolongs the time required for solidification of the aromatic bisphosphate in a melted state after the reaction or makes it difficult to solidify the aromatic bisphosphate. Also, the triaryl phosphate produced as a by-product is not preferable because it is poor in heat resistivity and causes plate-out at the time of molding the resin, contaminating the surface of the obtained molded article or degrading the appearance.

In order to obtain an aromatic bisphosphate of high purity, it is necessary to lower the content of these by-products. However, there were no processes that could reduce the content of these by-products simultaneously.

The above-described method (2), i.e. the process of preparing an aromatic bisphosphate having a steric hindrance group at its ortho position, is disclosed in the U.S. Pat. No. 5,420,327. In an Example of the above U.S. patent, an aromatic bisphosphate having a purity of 85.0 to 93.9% as measured by High Pressure Liquid Chromatography (HPLC) is obtained by reacting a little excess amount of 2,6-xylenol with phosphorus oxychloride to prepare bis(2,6-xylenyl) phosphorochloridate and reacting the obtained reaction mixture with hydroquinone without subjecting the reaction mixture to separation by distillation. However, the above U.S. patent does not mention the molar ratio nor the composition ratio of the by-products in the reaction of the aromatic monohydroxy compound with phosphorus oxychloride.

Japanese Unexamined Patent Publication (Kokai) No. HEI 8(1996)-143584 discloses a process of preparing a diarylphosphorohalidate compound of high purity by reacting 2,6-xylenol with phosphorus oxyhalide in the presence of a nitrogen-containing heterocyclic compound catalyst. However, the above Japanese article does not mention a purification process by distillation.

SUMMARY OF THE INVENTION

The purpose of the present invention is to provide a process of preparing aromatic bisphosphates of high purity from which crystalline powders can be easily obtained.

The inventors of the present invention have made a thorough research for solving the above-mentioned problems and have found out the following.

Namely, it has been found out that an aromatic bisphosphate of high purity can be prepared by reacting an aromatic monohydroxy compound with a little excess amount of phosphorus oxyhalide and subjecting the obtained reaction mixture to a distillation treatment so as to remove the by-products other than the object compound.

Accordingly, the present invention provides a process for preparing aromatic bisphosphates, comprising: a first step of reacting an aromatic monohydroxy compound having a steric hindrance group at the ortho position, with a phosphorus oxyhalide in the presence of a Lewis acid catalyst (a) to yield a reaction mixture containing diarylphosphorohalidate, and a second step of reacting the reaction mixture of the first step with an aromatic dihydroxy compound in the presence of a Lewis acid catalyst (b) to obtain an aromatic bisphosphate, wherein the aromatic monohydroxy compound and the phosphorus oxyhalide are reacted in a molar ratio of 2.0:1.0–1.1 in the first step, and the reaction mixture of the first step is subjected to a distillation treatment before the reaction of the second step, thereby obtaining the aromatic bisphosphate of high purity.

DETAILED DESCRIPTION OF THE PREFERRED EMBODIMENTS

Figure 1:
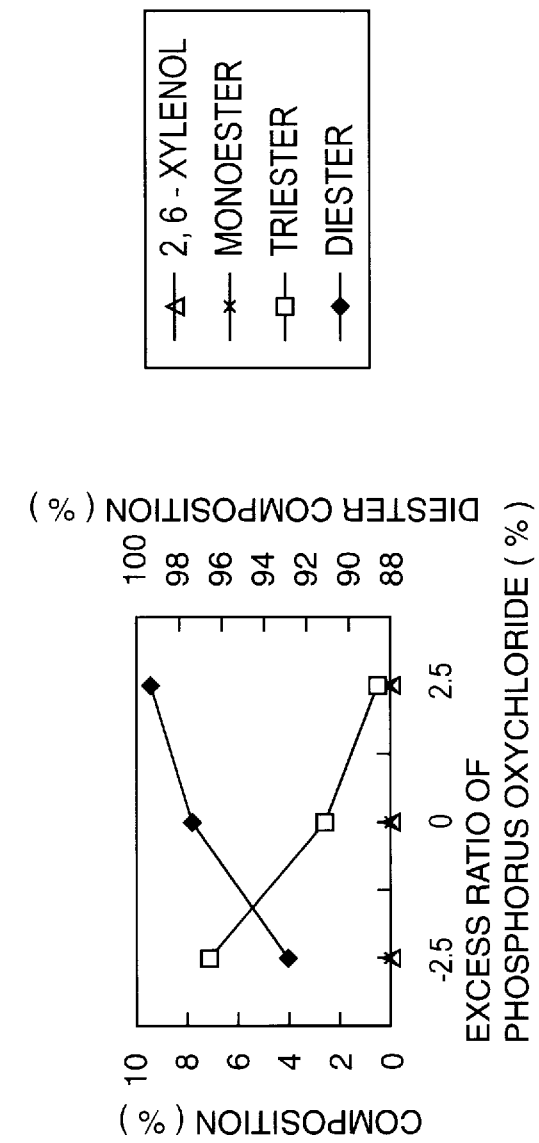
FIG. 1 is a view showing a composition ratio (excluding the solvent) as analyzed by chromatography on the reaction product distilled after the reaction according as the excess ratio of the phosphorus oxychloride is varied in the first step.

The above-mentioned process of preparing aromatic bisphosphates according to the present invention will be hereinafter explained in detail using chemical formulas.

In the first step, an aromatic monohydroxy compound having a steric hindrance group at its ortho position represented by the following formula (I):

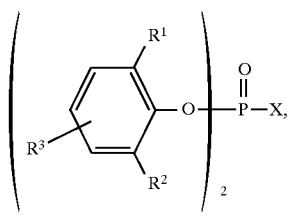

(wherein $R^1$ and $R^2$ are, the same or different, a lower alkyl group; and $R^3$ is a hydrogen atom or a lower alkyl group) is reacted with phosphorus oxyhalide in the presence of a Lewis acid catalyst (a) with the molar ratio of the aromatic monohydroxy compound to the phosphorus oxyhalide being 2.0:1.0–1.1 so as to obtain a reaction mixture containing a diarylphosphorohalidate represented by the following formula (II):

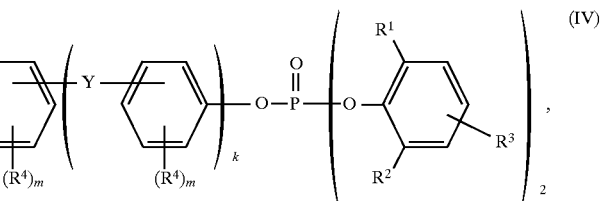

wherein the definition of the substituents $R^1$, $R^2$ and $R^3$ is the same as that of the formula (I); and X is a halogen atom.

The obtained reaction mixture is then distilled for obtaining the diarylphosphorohalidate of high purity.

In the second step, the diarylphosphorohalidate of high purity is reacted with an aromatic dihydroxy compound represented by the following formula (III):

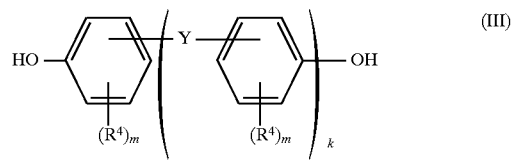

(wherein $R^4$ is a hydrogen atom or a lower alkyl group; Y is a bonding arm, —$CH_2$—, —$C(CH_3)_2$—, —S—, —$SO_2$—, —O—, —CO— or N=N—; k is 0 or 1; and m is an integer of 0 to 4) in the presence of a Lewis catalyst (b) so as to prepare an aromatic bisphosphate of high purity represented by the following formula (IV):

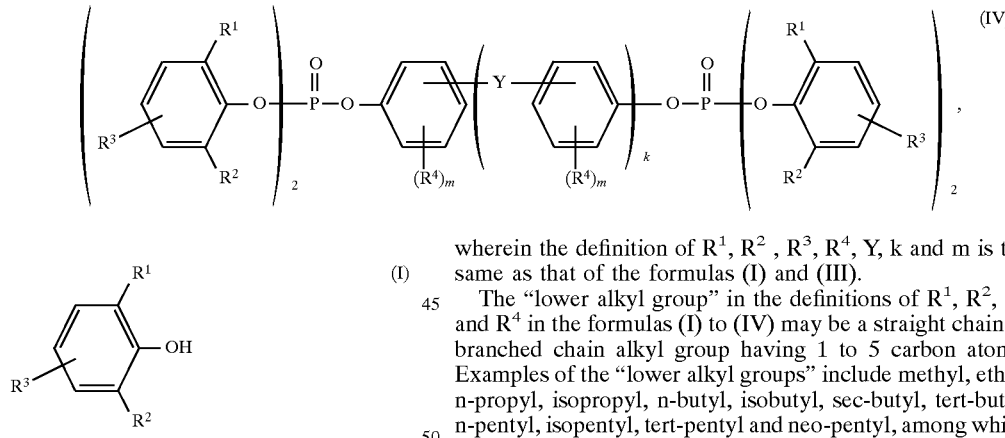

wherein the definition of $R^1$, $R^2$, $R^3$, $R^4$, Y, k and m is the same as that of the formulas (I) and (III).

The "lower alkyl group" in the definitions of $R^1$, $R^2$, $R^3$ and $R^4$ in the formulas (I) to (IV) may be a straight chain or branched chain alkyl group having 1 to 5 carbon atoms. Examples of the "lower alkyl groups" include methyl, ethyl, n-propyl, isopropyl, n-butyl, isobutyl, sec-butyl, tert-butyl, n-pentyl, isopentyl, tert-pentyl and neo-pentyl, among which methyl is preferable.

The aromatic monohydroxy compound for use in the present invention may be a compound represented by the formula (I), which may be, for example, 2,6-xylenol or 2,4,6-trimethylphenol.

The phosphorus oxyhalide for use in the present invention may be phosphorus oxychloride or phosphorus oxybromide, among which phosphorus oxychloride is preferable.

The aromatic dihydroxy compound for use in the present invention may be a compound represented by the formula (III), which may be, for example, hydroquinone, resorcin, pyrocatechol, 4,4'-biphenol, 2,2',6,6'-tetramethyl-4,4'-biphenol, bisphenol A, bisphenol S or bisphenol F, among which hydroquinone, resorcin and 4,4'-biphenol are preferable examples.

The Lewis acid catalyst (a) for use in the reaction of the first step of the present invention may be, for example, aluminum chloride, magnesium chloride, titanium chloride, antimony pentachloride, zinc chloride or tin chloride, among which magnesium chloride is preferable. A mixture of two or more of these compounds may also be used as the catalyst.

The Lewis acid catalyst (b) for the second step may be the catalyst remaining in the reaction mixture of the first step. However, it is possible to supplement further catalyst, which may be preferably aluminum chloride. Also, an amine such as triethylamine or tributylamine may be used as the catalyst.

In the first step, phosphorus oxyhalide is used in a ratio of 0.5 mole equivalent or more relative to the aromatic monohydroxy compound. In other words, phosphorus oxyhalide is used in an amount of 1.0 to 2.0 mole, preferably 1.0 to 1.1 mole, more preferably 1.0 to 1.05 mole, with respect to 2 mole of the aromatic monohydroxy compound. If the amount of phosphorus oxyhalide is too small, the amount of triaryl phosphate produced as a by-product will be large, which is not preferable.

In the second step, the aromatic dihydroxy compound is used in a ratio of 0.5 mole equivalent with respect to the diarylphosphorohalidate obtained in the first step.

The amount of catalyst to be used in the first step may be more than 0.1 wt %, preferably 0.5 to 2.0 wt % relative to the phosphorus oxyhalide.

The amount of catalyst to be used in the second step may be more than 0.1 wt %, preferably 0.5 to 5.0 wt % relative to the phosphorus oxyhalide used in the first step.

The reactions in the first and second steps maybe carried out at a temperature of 50° C. to 250° C., preferably 100° C. to 200° C. If the reaction temperature is lower than 50° C., the reactivity will be poor, which is not preferable. If the reaction temperature is higher than 250° C., by-products are produced by an ester interchange reaction, which is not preferable.

Also, the reaction system may be kept under reduced pressure so as to remove hydrogen halide produced as a by-product in the reaction away from the reaction system and to promote the reaction.

The reaction solvent is not necessarily needed and may be optionally used in the first step. The solvent to be used may be, for example, xylene, toluene, chlorobenzene or dichlorobenzene.

The reaction mixture obtained in the first step contains monoarylphosphorodihalidate at about 0.1 to 5% and a small amount of unreacted phosphorus oxyhalide as low boiling point components. These components are removed by the distillation treatment. The method for distillation treatment may be a conventional one such as simple distillation or rectification as long as the phosphorus oxyhalide or monoarylphosphorodihalidate which are low boiling point components can be cut out by distillation. Specifically, thin film distillation is preferable and industrially advantageous because it can efficiently remove only the low boiling point components.

The thin film distillation apparatus may be a commercially available one. For example, a Wiped Film Evaporator (manufactured by Shinko Pantec Co., Ltd. in Japan) or a Shell & Tube type Heat Exchanger (manufactured by Tokai Carbon Co., Ltd. in Japan) may be used as the thin film distillation apparatus.

Figure 6:
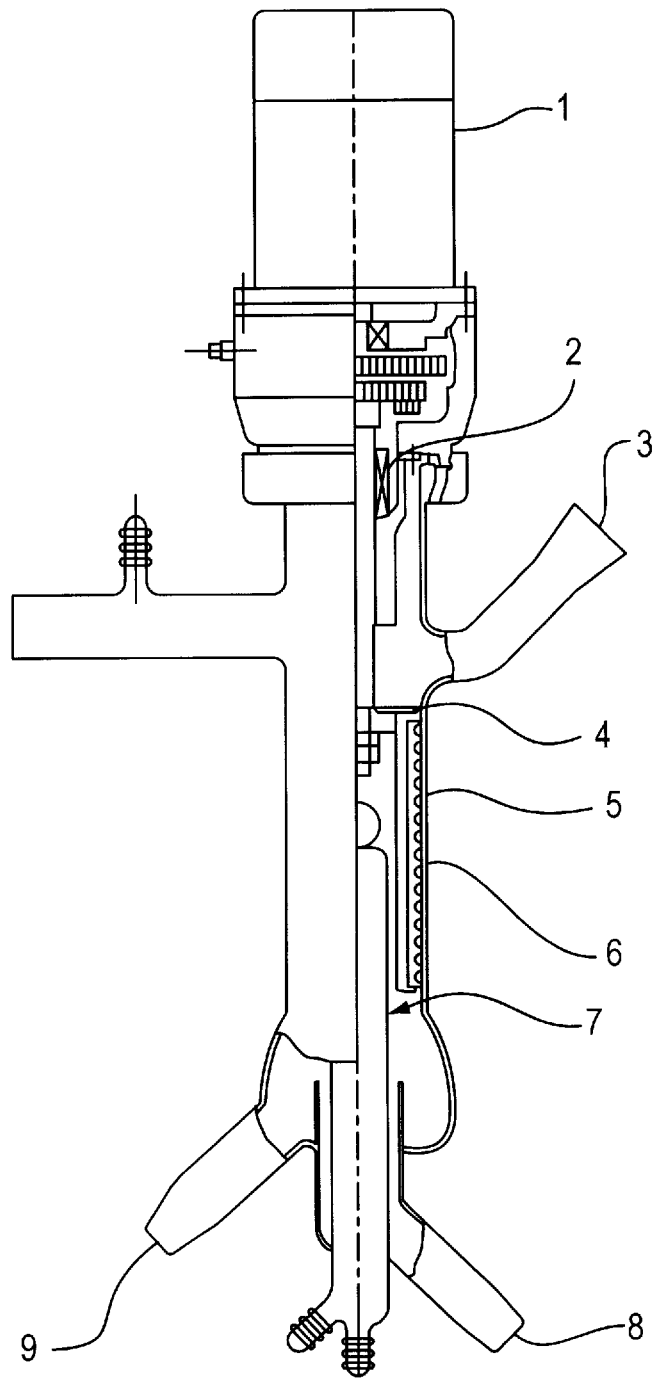
FIG. 6 is a schematic view of a thin film distillation apparatus that can be used in the present invention.

FIG. 6 is a schematic view of a Wiped Film Evaporator as an example of the above thin film distillation apparatus. The Evaporator shown in FIG. 6 includes a rotor (4) rotated by driving force of a geared motor (1), a mechanical seal (2) capable of high vacuum sealing, a wiper (6) which is mounted on the rotor (4) and slides on the inside of a glass still (5), and nozzles. The liquid to be processed is supplied from a feeding nozzle (3) and evaporates on an evaporation surface (not shown). Distillate liquid containing the low boiling point components condensed in an internal condenser (7) is discharged from a distillate nozzle (8), while residual liquid containing the high boiling point components is discharged from a residue nozzle (9).

In the second step, impurities such as the catalyst in the reaction products are removed by a conventional washing process after the reaction is completed. Removal of impurities can be achieved by, for example, contacting the reaction product with an aqueous acid solution such as aqueous hydrochloric acid solution to extract the impurities to the aqueous solution side.

At this stage, an organic solvent may be added for preventing the aromatic bisphosphate from being solidified. The organic solvent to be used here may be preferably a solvent in which the solubility of the bisphosphate is high. The organic solvent may be, for example, toluene, xylene, chlorobenzene or dichlorobenzene, but it is not specifically limited thereto. Also, amixture of these solvents maybe used as well.

The temperature at the time of contacting with the aqueous acid solution is within the range from the room temperature up to the boiling point of the solution. The contact is usually performed within the range of 30° C. to 120° C. The amount of the organic solvent to be used may be any amount as long as at least the aromatic bisphosphate is not deposited at the temperature of contact.

The washed mixture maybe cooled to precipitate crystals, which are separated by filtration; or the washed mixture is subjected to removal of water dissolved or dispersed in the washed mixture and then cooled to precipitate crystals, followed by filtration. Alternatively, after the solvent is removed under reduced pressure, the aromatic bisphosphate in a melted state is cooled, solidified, and made into powders with a flaker or a kneader. The latter is industrially preferable.

The obtained crystals may be dried as they are for use. Alternatively, the obtained crystals may be dried after the crystals are washed with a solvent such as water, methanol or ethanol which substantially does not dissolve the aromatic diphosphate.

The aromatic bisphosphate of high purity obtained by the production process according to the present invention can be used as a fire retardant, an antioxidant and a plasticizer for a thermoplastic resin or a thermosetting resin. The obtained aromatic bisphosphate is advantageous because it does not decrease the physical properties of the resin so much by addition.

Preferable examples of the thermoplastic resins include chlorinated polyethylene, polyethylene, polypropylene, polybutadiene, styrene resin, high-impact polystyrene, polyvinyl chloride, ACS resin, AS resin, ABS resin, modified polyphenylene oxide, polymethyl methacrylate, polyamide, polyester, polycarbonate, polyphenylene sulfide, polyethylene sulfide, polyimide, polyetheretherketone, polyether sulfone, polysulfone, polyallylate, polyetherketones, polyethernitrile, polythioether sulfone, polybenzimidazole, polycarbodiimide, liquid crystalline polymer and composite plastics. Preferable examples of tne thermosetting resins include polyurethane, phenol resin, melamine resin, urea resin, unsaturated polyester resin and diallyl phthalate resin. One of these resins may be singly used. Alternatively, two or more of these resins may be used in combination.

The above resins may optionally contain various kinds of additives such as other fire retardants, antioxidants, fillers and lubricants in accordance with the needs. The kind and amount of the aromatic bisphosphate to be used is suitably determined in accordance with the kind of the resin and the required degree of fire retardancy. Typically, the aromatic bisphosphate is used in a ratio of 0.1 to 100 parts by weight with respect to 100 parts by weight of the resin.

A fire retardant molded article may be obtained by kneading and molding the above resin, the aromatic bisphosphate and, optionally, the above additive by a conventional process.

The aromatic bisphosphate is given to the resin by, for example, (a) adding the aromatic bisphosphate together with monomers to be supplied in bulk polymerization, (b) adding the aromatic bisphosphate during the final stage of the reaction in the bulk polymerization, (c) adding the aromatic bisphosphate at the time of molding the resin or (d) applying the aromatic bisphosphate as a solution or dispersion on the surface of the resin such as a film or a fiber.

In view of the operativity in adjusting the resin composition, the fire retardant is preferably provided in powder form, which exhibits a good effect in kneading the fire retardant with resin. The aromatic bisphosphate of high purity prepared according to the present invention is in the form of crystalline powders of 95% or more purity and can be suitably used for kneading with the resin.

Moreover, the aromatic bisphos hate prepared according to the present invention is excellent in temperature stability and has a property such as being capable of withstanding the molding and processing temperature for an engineering plastic or a highly functional plastic having a higher function.

EXAMPLES

The present invention will hereinafter be explained in detail by way of Examples, which are not to be construed as being intended to limit the scope of the present invention. The obtained compound was evaluated by the following testing process.

(Melting Point)

The test was conducted in accordance with the Japanese Industrial Standard (JIS) K-0064

(Purity)

The purity of the reaction product obtained at the first step was measured by FID method by gas chromatography (GC, using GC-14A manufactured by Shimadzu Corporation in Japan) after phenylating the unreacted chloro group.

The phenylation of the unreacted chloro group was carried out by collecting approximately 0.2 g of the reaction product obtained in the first step, adding approximately 5 g of phenylation reagent (phenol:triethylamine:xylene= 5:10:50 wt %), and reacting the mixture by refluxing under heating for 10 minutes. Subsequently, the reacted mixture was cooled in ice and the precipitated crystals were collected by filtration. The filtrate was directly subjected to gas chromatography analysis.

The following is a design and analysis conditions of the apparatus used for the above measurement.

| | |
|---|---|
| Sample | 1 µl |
| Column | 1 m |
| Loading | SE-52 |
| Weight Percentage | 10 wt % |

-continued

| | |
|---|---|
| Support | Chromosorb W |
| Mesh | 80–100 |
| Processing | AW-DMCS |
| Reference Column | Same as above |
| Column Temperature | Maintain 100° C. × 2 minutes → Raise temperature at 10° C./min → Maintain 280° C. × 5 minutes |
| Carrier gas | N₂ |
| Flow rate | 50 ml/minúatm |
| Hydrogen gas pressure | 0.6 kg/cm² |
| Air pressure | 0.6 kg/cm² |
| Detector | FID |
| Detector temperature | 280° C. |
| Injection temperature | 250° C. |

The purity of the reaction product obtained in the second step and the final product was measured by gel permeation chromatography (GPC using HLC-8020 manufactured by Tosoh Corporation in Japan, and HLC-8010 for data processing).

The analysis conditions are as shown below.

| | |
|---|---|
| Column | G1000HXL × 2 |
| Column size | Internal diameter 7.8 mm × 30 cm |
| Flow rate | 0.8 ml/min |
| Mobile phase | THF |
| Column Pressure Temperature | 60 kg/cm² |
| Oven | 40° C. |
| RI | 35° C. |
| Inlet | 35° C. |

(Solidifiability)

The solidifiability of the final product was judged from the state of solidification by performing the following operations.

First, 400 g of aromatic bisphosphate in a melted state (about 100° C.) was loaded into a one-liter flask equipped with a thermometer and a stirrer (HEIDON TYPE 3000H manufactured by Shinto Kagaku Kabushiki Kaisha in Japan) having a function of displaying a rotational speed. The loaded aromatic bisphosphate was cooled to 60° C. under agitation with the rotational speed of 100 rpm while the temperature was controlled with a hot water bath. Then, after 0.4 g of crystalline aromatic bisphosphate was added as a crystal nucleus, the rotational speed of the stirrer was adjusted to be 200 rpm. The time from the above adjustment to the stoppage of rotation of the stirring motor due to the solidification was measured as the time required for solidification. Also, the state of solidification was judged as shown below.

Complete solidification: State of uniform and complete solidification

Bad solidification: State of incomplete solidification after 10 minutes of stirring Example 1

Synthesis of tetrakis(2,6-xylyl)m-phenylene bisphosphate (the following formula) by use of a little excess amount of phosphorus oxychloride

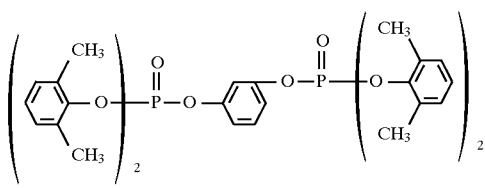

(First Step)

Into a four-neck flask equipped with a stirrer, a thermometer, a dropping funnel and a condenser connected to a water scrubber were loaded 400.0 g (3.273 mol) of 2,6-xylenol, 256.4 g (1.670 mol) of phosphorus oxychloride, 61.6 g of xylene and 2.5 g of magnesium chloride. The temperature of the mixture was raised from room temperature to 120° C. in one hour for reaction and the mixture was left to stand at that temperature for 1.5 hours. Then, the temperature of the mixture was raised to 160° C. in 1.5 hours for further reaction. The mixture was stirred at that temperature for one hour. Finally, the reaction was completed by reducing the pressure to 400 Torr, yielding 601.5 g of the reaction mixture.

The obtained reaction mixture was divided into two, and 300 g of the reaction mixture was subjected to thin film distillation at 3 Torr and 160° C., thereby removing the solvent xylene and the low boiling-point components as initial distillate. The resultant was 90% of the initial weight. The thin film distillation apparatus used in this Example was a 2-03 type thin film distillation apparatus for room experiments manufactured by Shinko Pantec Co., Ltd. in Japan. FIG. 6 shows a view of the apparatus.

The initial distillate contained 29 g of xylene and 29 g of the other low boiling-point components. The obtained distillation residue weighed 241 g.

(Second Step)

To 238 g of the resultant after distillation were added 40.5 g (0.368 mol) of resorcin, 30 g of xylene and 5.4 g of aluminum chloride. Then, the temperature was raised to 160° C. in 1.5 hours, and the reaction was carried out at that temperature for 2 hours. The reaction was further carried out under a reduced pressure of 400 Torr for 4 hours.

(Purification Step: Removal of Solvent and Catalyst)

To the reaction mixture obtained in the second step, 230 g of xylene was added. The mixture was washed with 25 g of 10% aqueous hydrochloric acid solution and 75 g of water at 90° C. to remove the remaining catalyst and the like. Then, xylene was removed from the oil layer under reduced pressure and, further, low boiling point components were removed by steam distillation under reduced pressure of 50 Torr at 130° C. for 2 hours, yielding 252 g of tetrakis(2,6-xylyl)m-phenylene bisphosphate. The obtained compound solidified speedily during the process of cooling to room temperature.

The obtained compound was evaluated by the above process.

The result is shown in Table 1.

Comparison Example 1

The same steps as in the above Example 1 were carried out except that the distillation operation was not performed in the first step.

The remaining one (300.0 g) of the reaction mixture divided into two in the first step of the Example 1 was used without distillation in the reaction of the second step. The result is shown in Table 1.

This Example compared with the Example 1 shows that, if the monoaryl dichloridate is contained in a larger amount, the oligomeric phosphate will be contained in an amount as high as 7.2% in the final product. Accordingly, the obtained product did not solidify easily.

Example 2

The same steps as in the Example 1 were carried out except that the phosphorus oxychloride was used in a stiochiometrically equivalent amount to 2,6-xylenol.

The result shows that, by a stoichiometrically equivalent reaction, the aromatic triphosphate is produced in a little larger amount although the production of the oligomeric phosphate can be prevented by distillation.

Comparison Example 2

The same steps as in the above Example 2 were carried out except that the distillation operation was not performed in the first step.

The remaining one (300.0 g) of the reaction mixture divided into two in the first step of the Example 2 was used without distillation in the reaction of the second step. The result is shown in Table 1.

The result shows that the oligomeric phosphate was produced in a larger amount because the distillation operation was not performed, thereby reducing the purity of the final product. Accordingly, the solidification speed also decreased.

Comparison Examples 3 and 4

The same steps as in the Example 1 and the Comparison Example 1 were carried out except that the phosphorus oxychloride was used in an amount which is by 2.5% smaller than the theoretical value for reaction. The result is shown in Table 1.

The result shows that, if the amount to be used of phosphorus oxychloride is smaller than the theoretical value, a large amount of aromatic triester is produced although the production of oligomeric phosphate is inhibited in the reaction. Therefore, the melting point was lower than that of other cases and the solidification was difficult.

Figure 2:
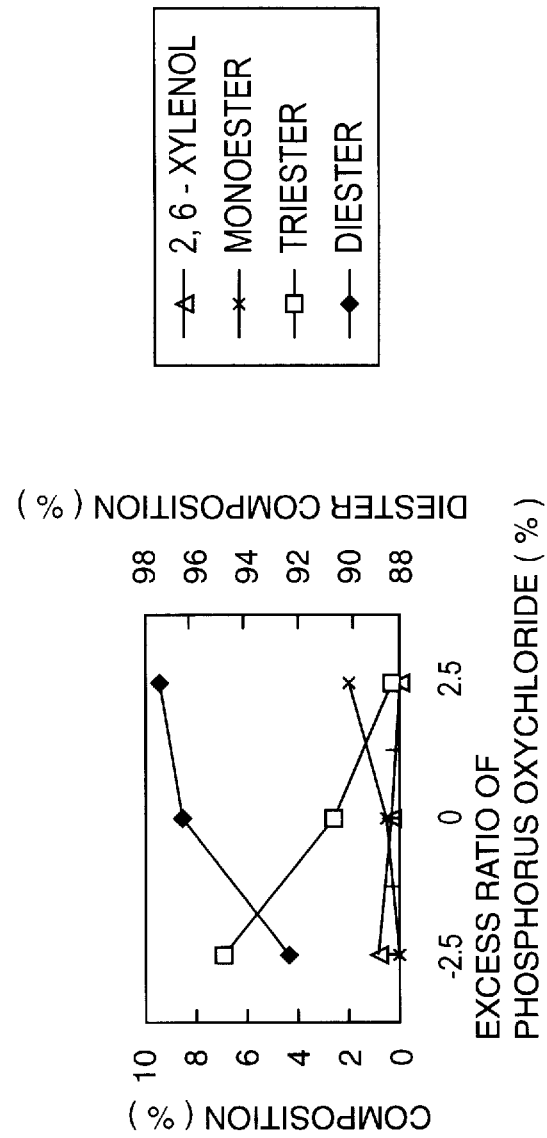
FIG. 2 is a view showing a composition ratio (excluding the solvent) as analyzed by chromatography on the reaction product not distilled after the reaction according as the excess ratio of the phosphorus oxychloride is varied in the first step.

FIGS. 1 and 2 show a composition ratio (excluding the solvent) as analyzed by chromatography on the reaction product after the reaction according as the excess ratio of the phosphorus oxychloride is varied in the first step. FIG. 1 shows a case in which the distillation treatment is performed, whereas FIG. 2 shows a case in which the distillation treatment is not performed. These Figures show that the reaction product obtained by reaction with a little excess amount of phosphorus oxychloride in the first step and subsequent distillation contains a smaller amount of by-products. The term "GC composition" in the Figures represents a composition by analysis with gas chromatography.

Figure 3:
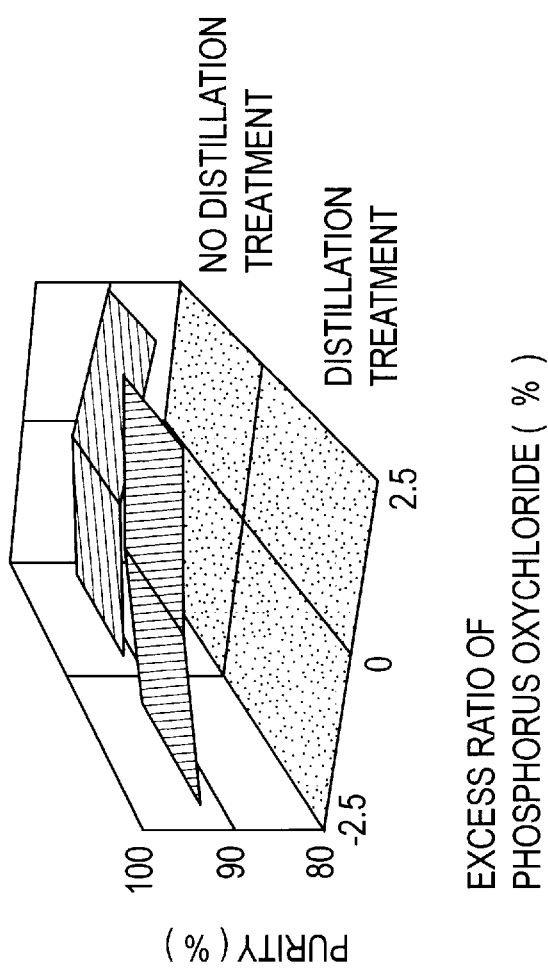
FIG. 3 is a view showing an effect of the excess ratio of the phosphorus oxychloride on the purity of the final product (aromatic bisphosphate).

FIG. 3 shows an effect of the excess ratio of the phosphorus oxychloride on the purity of the final product (aromatic bisphosphate). This shows that the reaction product obtained by reaction with a little excess amount of phosphorus oxychloride in the first step and subsequent distillation treatment yields a high purity of the final product (aromatic bisphosphate). The term "GPC composition" in the Figure represents a composition by analysis with gel permeation chromatography.

Figure 4:
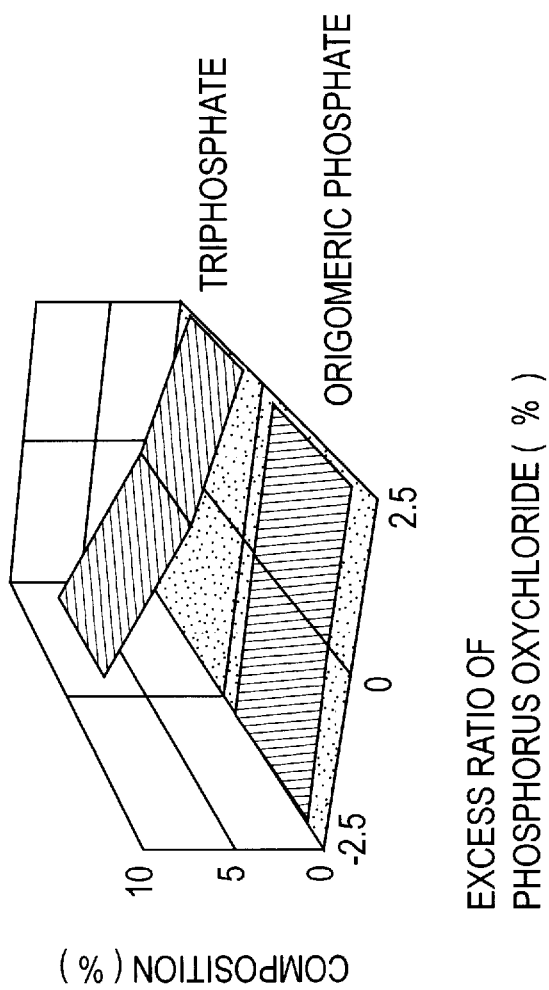
FIG. 4 is a view showing an effect of the excess ratio of the phosphorus oxychloride on the ratio of the by-products (oligomeric phosphate and triphosphate) contained in the product when the reaction mixture obtained in the first step is distilled.
Figure 5:
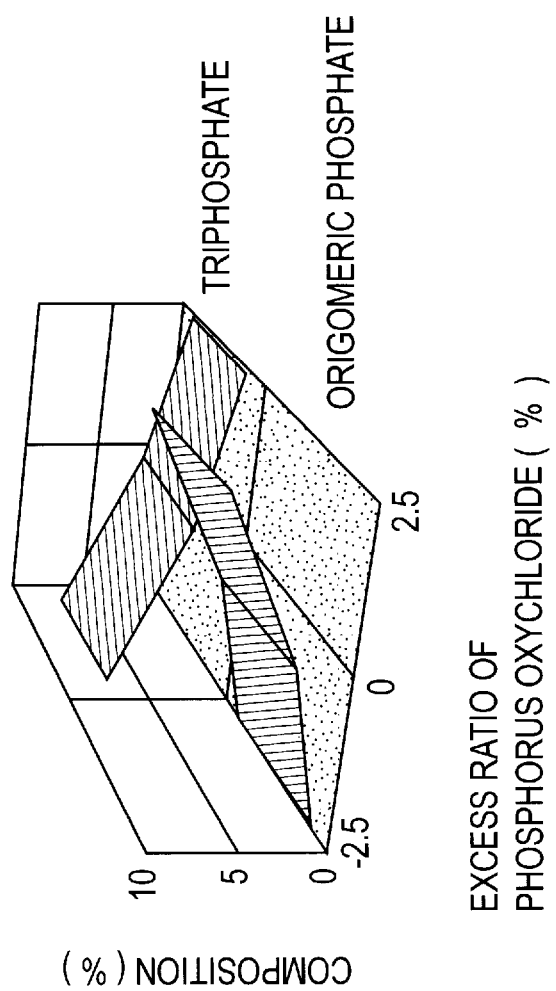
FIG. 5 is a view showing an effect of the excess ratio of the phosphorus oxychloride on the ratio of the by-products (oligomeric phosphate and triphosphate) contained in the product when the reaction mixture obtained in the first step is not distilled.

FIGS. 4 and 5 show the ratio of by-products (oligomeric phosphate and triphosphate) contained in the product according as the excess ratio of the phosphorus oxychloride is varied in the first step. FIG. 4 shows acase inwhich the distillation treatment is performed after the first step, whereas FIG. 5 shows a case in which the distillation treatment is not performed. These Figures show that the reaction product obtained by reaction with a little excess amount of phosphorus oxychloride in the first step and subsequent distillation contains a smaller amount of by-products.

According to the present invention, the amount of oligomeric phosphate and aromatic triphosphate contained in the aromatic bisphosphate will be extremely small, so that the aromatic bisphosphate will be highly purified and the solidification speed will be high. Therefore, the process of solidifying and making the product into powders after the reaction will be extremely simplified, making it easier to handle the product. Moreover, there will be no plate-out at the time of molding the resin. This leads to improved commercial value in the molded article.

TABLE 1

|  | Example. 1 | Comp. 1 | Example. 2 | Comp. 2 | Comp. 3 | Comp. 4 |
|---|---|---|---|---|---|---|
| FIRST STEP | | | | | | |
| LOAD | | | | | | |
| 2,6-xylenol | 400.0 g (3.27 mol) | | <---- | | <---- | |
| phosphorus oxychloride | 256.4 g (1.67 mol) | | 250.1 g (1.63 mol) | | 243.8 g (1.59 mol) | |
| magnesium chloride | 2.5 g | | <---- | | <---- | |
| xylene | 61.6 g | | <---- | | <---- | |
| distillation | performed | none | performed | none | performed | none |
| GC composition | | | | | | |
| 2,6-xylenol | 0.0 | 0.0 | 0.0 | 0.3 | 0.0 | 0.8 |
| mnonoester | 0.2 | 2.1 | 0.0 | 0.5 | 0.0 | 0.0 |
| diester | 99.4 | 97.5 | 97.4 | 96.6 | 92.9 | 92.4 |
| triester | 0.4 | 0.4 | 2.6 | 2.6 | 7.1 | 6.8 |
| SECOND STEP | | | | | | |
| LOAD | | | | | | |
| resorcin | 40.5 | 45.0 | 40.0 | 43.8 | 38.1 | 42.6 |
| aluminum chloride | 5.4 | <---- | <---- | <---- | <---- | <---- |
| GPC composition (reacted) | | | | | | |
| oligomeric phosphate | 0.4 | 7.2 | 0.1 | 2.1 | 0.1 | 0.2 |
| bisphosphate | 98.2 | 91.3 | 96.0 | 94.0 | 92.1 | 91.0 |
| half ester | 0.8 | 1.0 | 0.9 | 0.9 | 0.8 | 1.0 |
| triester | 0.4 | 0.4 | 2.7 | 2.6 | 6.9 | 7.0 |
| monoester | 0.1 | 0.1 | 0.1 | 0.1 | 0.1 | 0.0 |
| 2,6-xylenol | 0.1 | 0.0 | 0.2 | 0.3 | 0.0 | 0.8 |
| PURIFYING STEP | | | | | | |
| GPC composition (purified) | | | | | | |
| oligomeric phosphate | 0.4 | 7.2 | 0.1 | 2.2 | 0.1 | 0.2 |
| bisphosphate | 98.4 | 91.4 | 96.3 | 94.3 | 92.2 | 91.8 |
| half ester | 0.8 | 1.0 | 0.9 | 0.9 | 0.8 | 1.0 |
| triester | 0.4 | 0.4 | 2.7 | 2.6 | 6.9 | 7.0 |
| monoester | 0.0 | 0.0 | 0.0 | 0.0 | 0.0 | 0.0 |
| 2,6-xylenol | 0.0 | 0.0 | 0.0 | 0.0 | 0.0 | 0.0 |
| PROPERTY | | | | | | |
| melting point (°C.) | 95.6–95.7 | 88.5–93.0 | 95.1–95.3 | 95.1–95.3 | 89.5–92.8 | 89.5–92.8 |
| solidification speed (min) | 5 | >25 | 6 | 8 | >25 | >25 |
| solidifiability | completely solidified | bad | completely solidified | completely solidified | bad | bad |

(NOTES)
Monoester: 2,6-xylyl phosphorodichloridate
Diester: bis(2,6-xylyl) phosphorochloridate
Triester: tris(2,6-xylyl) phosphate
Bisphosphate: tetrakis(2,6-xylyl)-m-phenylene bisphosphate
Half ester: bis(2,6-xylyl)-m-hydroxyphenyl phosphate

What we claim is:

1. A process for preparing aromatic bisphosphates, comprising:

a first reaction comprising reacting an aromatic monohydroxy compound having a steric hindrance group at an ortho position, with a phosphorus oxyhalide in the presence of a Lewis acid catalyst (a) to yield a reaction mixture containing diarylphosphorohalidate, wherein the aromatic monohydroxy compound and the phosphorus oxyhalide are reacted in a molar ratio of 2.0:1.0–1.1;

subjecting the reaction mixture of the first reaction to a distillation treatment in a thin film distillation apparatus to remove by-products; and subjecting the reaction mixture after the distillation treatment to a second reaction including reaction with an aromatic dihydroxy compound in the presence of a Lewis acid catalyst (b) to obtain an aromatic bisphosphate of high purity.

2. The process for preparing aromatic bisphosphates of claim 1, wherein the aromatic monohydroxy compound has the following formula (I):

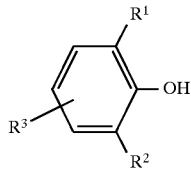

wherein $R^1$ and $R^2$ are, the same or different, a lower alkyl group; and $R^3$ is selected from the group consisting of hydrogen and a lower alkyl group.

3. The process for preparing aromatic bisphosphates of claim 1, wherein the aromatic monohydroxy compound is selected from the group consisting of 2,6-xylenol and 2,4,6-trimethylphenol.

4. The process for preparing aromatic bisphosphates of claim 1, wherein the phosphorus oxyhalide is selected from the group consisting of phosphorus oxychloride and phosphorus oxybromide.

5. The process for preparing aromatic bisphosphates of claim 1, wherein the phosphorus oxyhalide comprises phosphorus oxychloride.

6. The process for preparing aromatic bisphosphates of claim 5, wherein the molar ratio of the aromatic monohydroxy compound to the phosphorus oxychloride is 2.0:1.0–1.05.

7. The process for preparing aromatic bisphosphates of claim 1, wherein the first reaction is performed at a temperature of 50° to 250° C.

8. The process for preparing aromatic bisphosphates of claim 7, wherein the first reaction is performed at a temperature of 100° to 200° C.

9. The process for preparing aromatic bisphosphates of claim 1, wherein the Lewis acid catalyst (a) is selected from the group consisting of magnesium chloride, aluminum chloride, titanium chloride, antimony pentachloride, zinc chloride, tin chloride, and mixtures thereof.

10. The process for preparing aromatic bisphosphates of claim 9, wherein the Lewis acid catalyst (a) comprises magnesium chloride.

11. The process for preparing aromatic bisphosphates of claim 1, wherein the Lewis acid catalyst (a) is added in a ratio of 0.5 to 2.0 wt % relative to the phosphorus oxyhalide.

12. The process for preparing aromatic bisphosphates of claim 1, wherein the aromatic dihydroxy compound has the following formula (III):

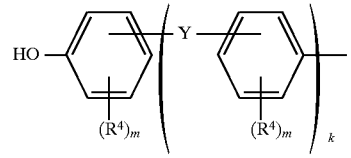

wherein $R^4$ is selected from the group consisting of hydrogen and a lower alkyl; Y is selected from the group consisting of a direct bond, —$CH_2$—, —$C(CH_3)_2$—, —S—, —$SO_2$—, —O—, —CO—, and —N=N—; k is selected from the group consisting of 0 and 1; and m is an integer of 0 to 4.

13. The process for preparing aromatic bisphosphates of claim 12, wherein the aromatic dihydroxy compound is selected from the group consisting of hydroquinone and 4,4'-biphenol.

14. The process for preparing aromatic bisphosphates of claim 1, wherein the aromatic dihydroxy compound is used in a ratio of 0.5 mole equivalent relative to the diarylphosphorohalidate in the reaction mixture.

15. The process for preparing aromatic bisphosphates of claim 1, wherein the second reaction is performed at a temperature of 50° to 250° C.

16. The process for preparing aromatic bisphosphates of claim 15, wherein the second reaction is performed at a temperature of 100° to 200° C.

17. The process for preparing aromatic bisphosphates of claim 1, wherein the Lewis acid catalyst (b) is selected from the group consisting of magnesium chloride, aluminum chloride, titanium chloride, antimony pentachloride, zinc chloride, tin chloride, and mixtures thereof.

18. The process for preparing aromatic bisphosphates of claim 17, wherein the Lewis acid catalyst (b) is aluminum chloride.

19. The process for preparing aromatic bisphosphates of claim 1, wherein the Lewis acid catalyst (b) is added in a ratio of 0.5 to 5.0 wt % relative to the phosphorus oxyhalide.

* * * * *

UNITED STATES PATENT AND TRADEMARK OFFICE
CERTIFICATE OF CORRECTION

PATENT NO. : 5,880,308
DATED : March 9, 1999
INVENTOR(S) : S. KAWATA et al.

It is certified that error appears in the above-identified patent and that said Letters Patent is hereby corrected as shown below:

At column 14, line 4 (claim 12, line 4) of the printed patent, change formula III from:

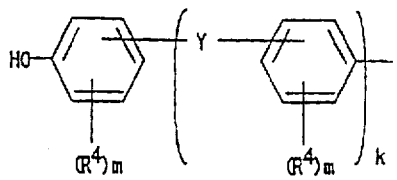

to:

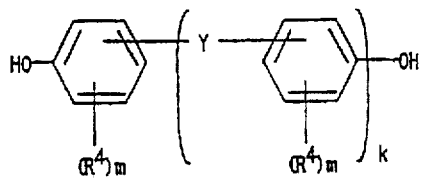

Signed and Sealed this

Ninth Day of May, 2000

Attest:

Q. TODD DICKINSON

*Attesting Officer*     *Director of Patents and Trademarks*